(12) United States Patent
Tojo et al.

(10) Patent No.: US 10,302,933 B2
(45) Date of Patent: May 28, 2019

(54) INSERTION APPARATUS

(71) Applicant: OLYMPUS CORPORATION, Tokyo (JP)

(72) Inventors: Ryo Tojo, Hachioji (JP); Hiromasa Fujita, Hachioji (JP); Eiji Yamamoto, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 195 days.

(21) Appl. No.: 15/184,068

(22) Filed: Jun. 16, 2016

(65) Prior Publication Data
US 2016/0291313 A1   Oct. 6, 2016

Related U.S. Application Data

(63) Continuation of application No. PCT/JP2014/081798, filed on Dec. 1, 2014.

(30) Foreign Application Priority Data

Dec. 19, 2013   (JP) .................. 2013-262617

(51) Int. Cl.
*A61B 1/00* (2006.01)
*A61B 34/20* (2016.01)
(Continued)

(52) U.S. Cl.
CPC ...... *G02B 23/2476* (2013.01); *A61B 1/00165* (2013.01); *G01B 11/18* (2013.01);
(Continued)

(58) Field of Classification Search
CPC ............ A61B 34/20; A61B 2034/2046; A61B 2034/2061; A61B 1/00165; A61B 1/00167; A61B 5/065; G02B 11/24; G02B 6/02395
(Continued)

(56) References Cited

U.S. PATENT DOCUMENTS

| | | | | |
|---|---|---|---|---|
| 5,321,257 A | * | 6/1994 | Danisch | G02B 6/02066 250/227.16 |
| 7,209,605 B2 | * | 4/2007 | Cantin | G01D 5/35383 374/E11.016 |

(Continued)

FOREIGN PATENT DOCUMENTS

| | | |
|---|---|---|
| JP | 2002-345729 A | 12/2002 |
| JP | 2003-52612 A | 2/2003 |

(Continued)

OTHER PUBLICATIONS

Extended Supplementary European Search Report dated Aug. 17, 2017 in European Patent Application No. 14 87 2393.5.
(Continued)

*Primary Examiner* — Aaron B Fairchild
(74) *Attorney, Agent, or Firm* — Scully, Scott, Murphy & Presser, P.C.

(57) ABSTRACT

An insertion apparatus includes a flexible insert section inserted into an insertion target and a curved-shape detection sensor which detects a curved shape of the insert section. The curved-shape detection sensor includes at least a core, a cladding, a coating, and a sensing part mechanically attached to the core and detecting the curved shape. The optical fiber is disposed at least in the insert section. The optical fiber includes at least one displacement restraint section which directly or indirectly restrains a displacement of the sensing part relative to the insert section.

11 Claims, 13 Drawing Sheets

(51) Int. Cl.
  *G01B 11/16* (2006.01)
  *G01B 11/24* (2006.01)
  *G02B 23/24* (2006.01)

(52) U.S. Cl.
  CPC .......... *G01B 11/24* (2013.01); *G02B 23/2469* (2013.01); *A61B 2034/2061* (2016.02)

(58) Field of Classification Search
  USPC .......................................................... 600/117
  See application file for complete search history.

(56) References Cited

U.S. PATENT DOCUMENTS

| | | | |
|---|---|---|---|
| 9,239,429 B2* | 1/2016 | Sakai | A61B 1/00165 |
| 9,435,639 B2* | 9/2016 | Fujita | G01B 11/18 |
| 10,016,120 B2* | 7/2018 | Fujita | A61B 1/00 |
| 2002/0183592 A1 | 12/2002 | Suzuki et al. | |
| 2007/0116415 A1 | 5/2007 | Kobayashi | |
| 2014/0222214 A1 | 8/2014 | Tojo et al. | |
| 2015/0335226 A1* | 11/2015 | Kuboi | A61B 1/00131 600/117 |
| 2015/0359419 A1* | 12/2015 | Hane | A61B 1/00002 600/117 |
| 2016/0007831 A1* | 1/2016 | Tojo | A61B 1/0051 600/103 |
| 2016/0073863 A1* | 3/2016 | Kuboi | G02B 23/2476 600/117 |
| 2016/0081761 A1* | 3/2016 | Kuboi | A61B 1/00004 600/424 |
| 2016/0327781 A1* | 11/2016 | Kuboi | A61B 1/07 |
| 2016/0360951 A1* | 12/2016 | Hane | G02B 23/26 |
| 2017/0020612 A1* | 1/2017 | Kuboi | G02B 23/26 |
| 2018/0028055 A1* | 2/2018 | Tojo | A61B 34/20 |
| 2018/0160882 A1* | 6/2018 | Kuboi | A61B 1/00 |
| 2018/0200000 A1* | 7/2018 | Takayama | A61B 34/20 |

FOREIGN PATENT DOCUMENTS

| | | |
|---|---|---|
| JP | 2007-44412 A | 2/2007 |
| JP | 2007-143600 A | 6/2007 |
| WO | 2013/054907 A1 | 4/2013 |

OTHER PUBLICATIONS

Chinese Office Action dated Sep. 7, 2017 received in 201480069005.8.

International Preliminary Report on Patentability together with the Written Opinion from related International Application No. PCT/JP2014/081798 dated Jun. 30, 2016.

International Search Report dated Feb. 24, 2015 issued in PCT/JP2014/081798.

Chinese Office Action dated Apr. 28, 2017 in Chinese Patent Application No. 201480069005.8.

* cited by examiner

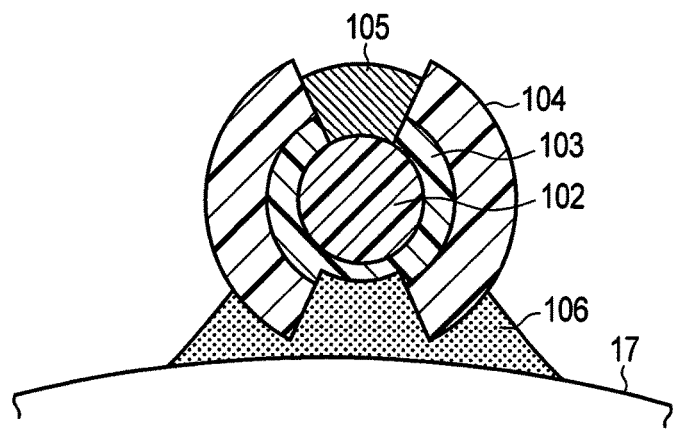
F I G. 14
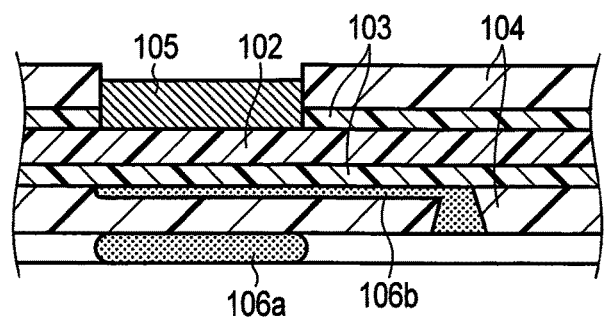
F I G. 15

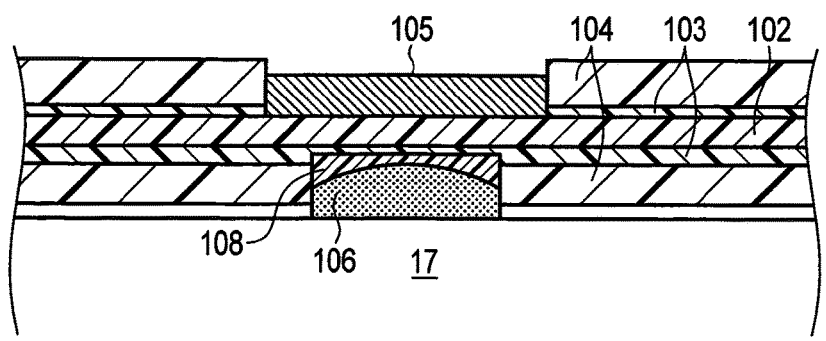
F I G. 18
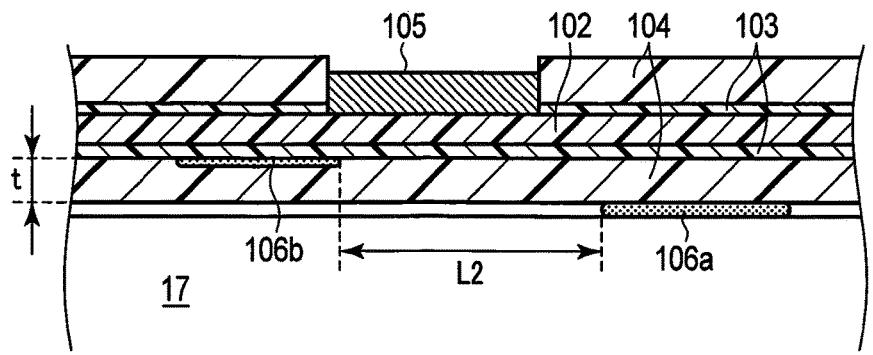
F I G. 19

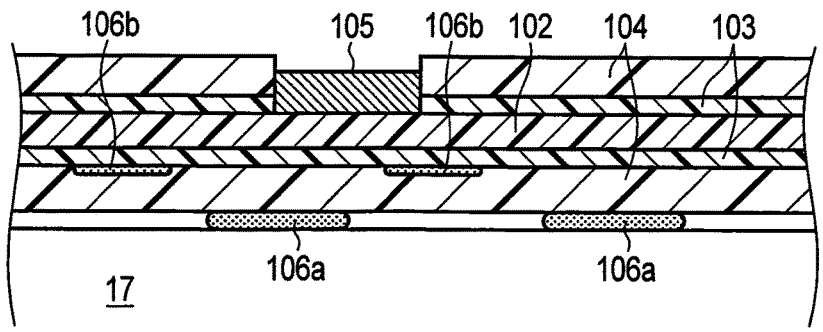
F I G. 20
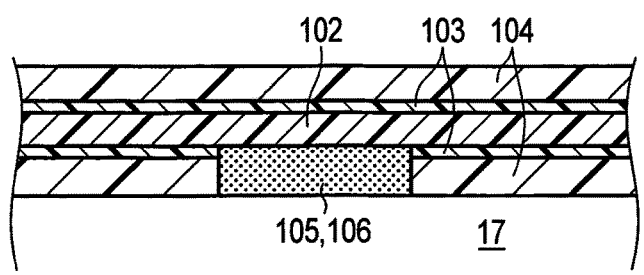
F I G. 21
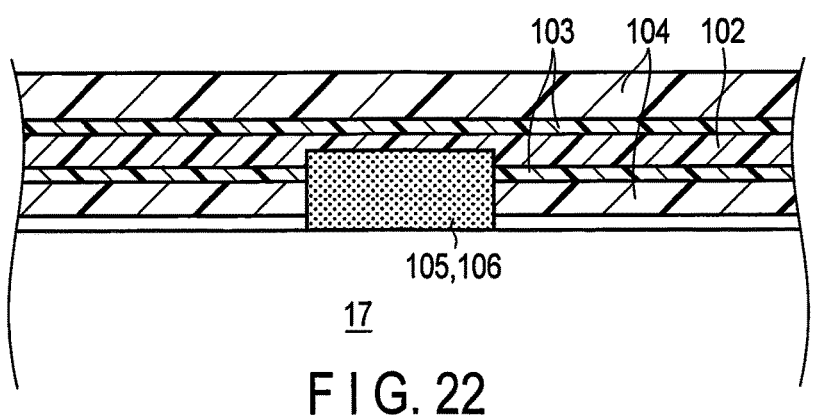
F I G. 22

INSERTION APPARATUS

CROSS-REFERENCE TO RELATED APPLICATIONS

This application is a Continuation Application of PCT Application No. PCT/JP2014/081798, filed Dec. 1, 2014 and based upon and claiming the benefit of priority from prior the Japanese Patent Application No. 2013-262617, filed Dec. 19, 2013, the entire contents of all of which are incorporated herein by references.

BACKGROUND OF THE INVENTION

1. Field of the Invention

The present invention relates to an insertion apparatus into which a curved-shape detection sensor is incorporated.

2. Description of the Related Art

It is known to incorporate a curved-shape detection sensor into an insertion apparatus (e.g. an endoscope) including an elongated insert section to be inserted into an insertion target and detect a curved shape (a curved angle and a curved direction) thereof.

For example, Jpn. Pat. Appln. KOKAI Publication No. 2003-52612 discloses an endoscope into which a curved-shape detection sensor is incorporated, wherein the curved-shape detection sensor includes a plurality of sensing parts for detecting a curved shape. The curved-shape detection sensor includes optical fibers including a core onto which light absorbers are formed only in a predetermined direction at portions from which a cladding is exposed. The curved-shape detection sensor detects a curved shape of the endoscope on the basis of the fact that the amount of light guided through the optical fibers varies with the curved angle and curved direction of the optical fibers. The curved direction is determined by means of a sensing part according to a light absorber which is formed in a predetermined direction. The optical fibers are not fixed to the proximal end of the endoscope and extend to cause a small wave such that they cannot be easily broken even though curvature appears repeatedly.

BRIEF SUMMARY OF THE INVENTION

One embodiment of the present invention is an insertion apparatus including a flexible insert section to be inserted into an insertion target; and a curved-shape detection sensor which detects a curved shape of the insert section, wherein the curved-shape detection sensor includes at least a core, a cladding covering the core, a coating covering the cladding, and a sensing part mechanically attached to the core and which contributes to detect the curved shape, the optical fiber is disposed at least in the insert section, and the optical fiber includes at least one displacement restraint section which directly or indirectly restrains a displacement of the sensing part relative to the insert section.

Advantages of the invention will be set forth in the description which follows, and in part will be obvious from the description, or may be learned by practice of the invention. The advantages of the invention may be realized and obtained by means of the instrumentalities and combinations particularly hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 14 is a cross-sectional view showing an optical fiber fixed to a channel tube by a displacement restraint section.

FIG. 15 is a longitudinal sectional view showing an optical fiber fixed to a channel tube by displacement restraint sections.

FIG. 18 is a longitudinal sectional view showing an optical fiber fixed to a channel tube by displacement restraint sections.

FIG. 19 is a longitudinal sectional view showing a relationship in position between two displacement restraint sections in the longitudinal direction of the optical fiber.

FIG. 20 is a longitudinal sectional view showing an optical fiber fixed to a channel tube by a plurality of displacement restraint sections.

FIG. 21 is a longitudinal sectional view showing an optical fiber in which a sensing part and a displacement restraint section are formed integrally as one unit.

FIG. 22 is a longitudinal sectional view showing an optical fiber in which a sensing part and a displacement restraint section are formed integrally as one unit.

DETAILED DESCRIPTION OF THE INVENTION

Embodiments of the present invention will be described below with reference to the drawings. Hereinafter, an endoscope will be described as one example of an insertion apparatus; however, the insertion apparatus is not limited to the endoscope but includes, for example, a catheter, forceps and a treatment tool.

Figure 1:
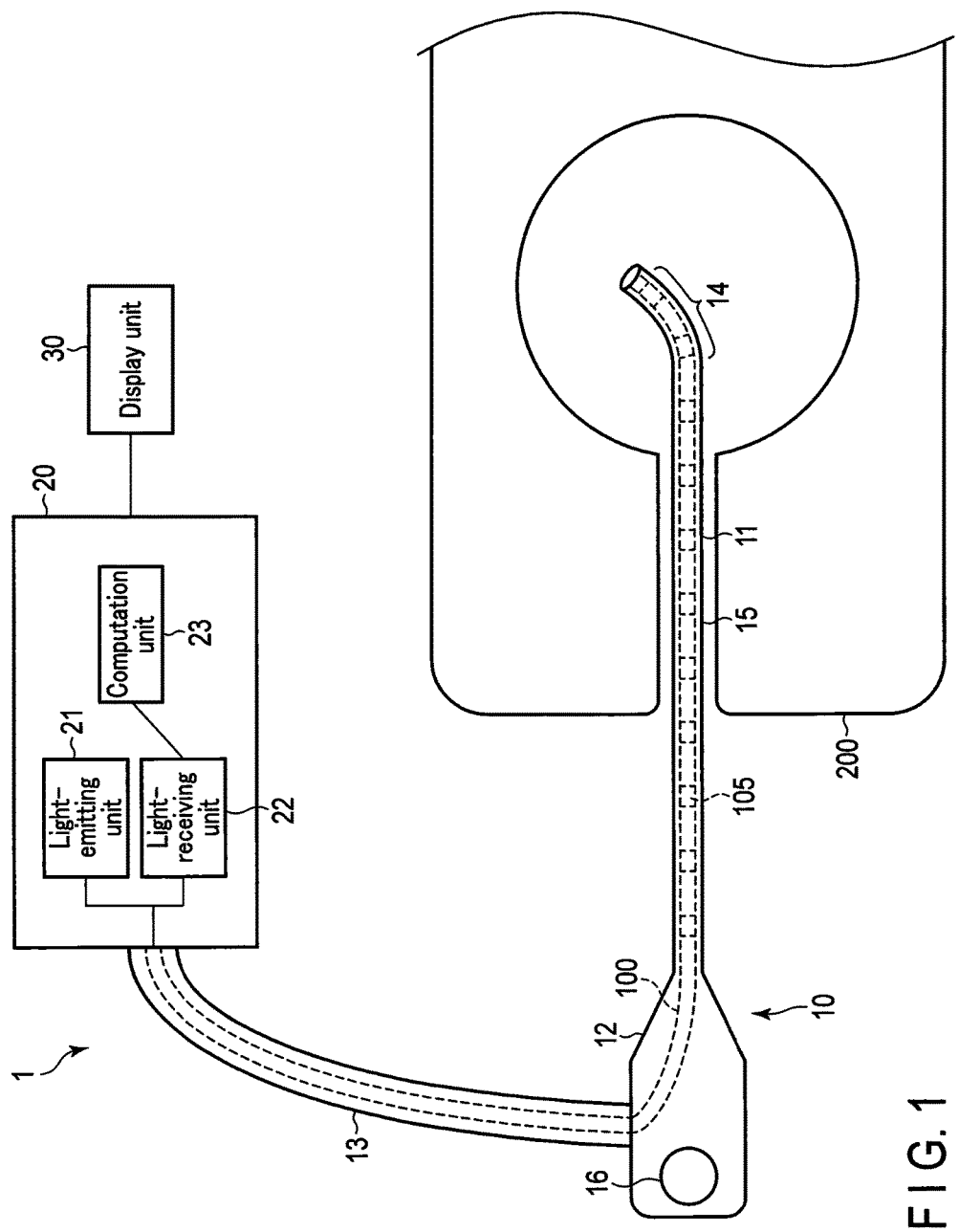
FIG. 1 is a diagram showing the overall configuration of an endoscope apparatus.

FIG. 1 is a diagram showing the overall configuration of an endoscope apparatus 1. The endoscope apparatus 1 includes an endoscope 10 into which a curved-shape detection sensor 100 is incorporated, an apparatus main body 20 connected to the endoscope 10, and a display unit 30 connected to the apparatus main body 20. The apparatus main body 20 includes a light-emitting unit 21 that supplies light to the curved-shape detection sensor 100, a light-receiving unit 22 that receives light returned from the curved-shape detection sensor 100, and a computation unit 23 that computes a curved shape of a curved portion 14 (described later) of the endoscope 10 on the basis of the amount of light received by the light-receiving unit 22. Though not shown, the apparatus main body 20 also includes, for example, a control unit that controls a predetermined function of one or more peripheral devices including the endoscope 10, which is connected to the apparatus main body 20.

[Endoscope]

The endoscope 10 includes a flexible insert section 11 to be inserted into an insertion target 200, an operation unit main body 12 coupled to the proximal end of the insert section 11, and a cord section 13 extending from the operation unit main body 12 and including optical fibers 101, an optical fiber 18 for illumination light and wiring 19 for image pickup elements, which will be describe later. The endoscope 10 is detachably connected to the apparatus main body 20 via the cord section 13 to communicate with the apparatus main body 20.

The insert section 11 is a long and narrow tubular portion on the distal-end side of the endoscope. The insert section 11 includes a curved portion 14 on its distal-end side and an elongated flexible tubular portion 15 on its proximal-end side. Though not shown, the distal end of the insert section 11 contains, for example, an observation optical system including an objective lens, an image pickup element which forms an optical image from the observation optical system and converts it into an electrical signal, and an illumination optical system including an illumination lens. The curved portion 14 is curved in a desired direction if an operator manually operates an operation knob 16 disposed on the operation unit main body 12. The flexible tubular portion 15 is curved along the curved shape of the insertion target 200.

Figure 2:
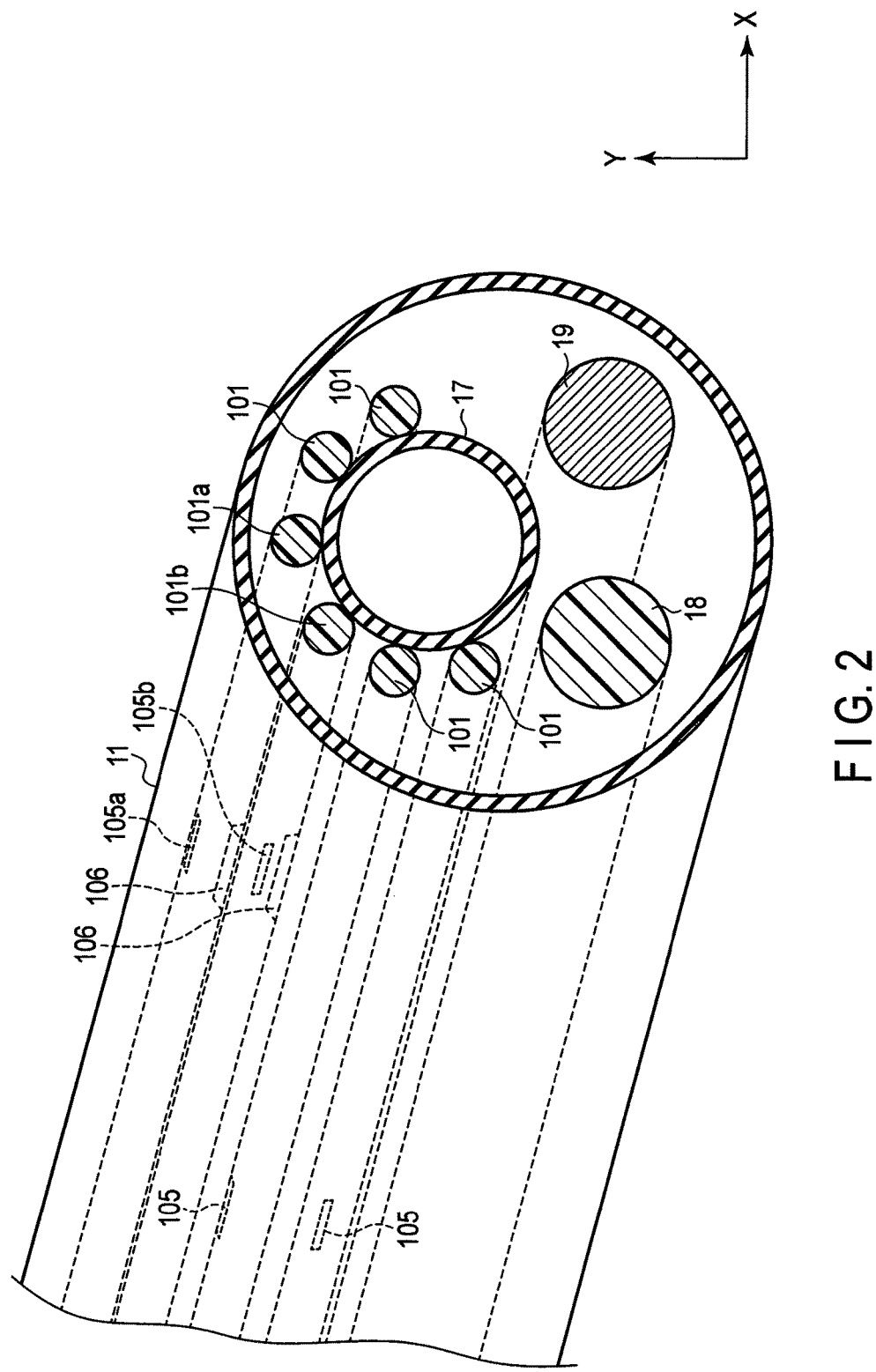
FIG. 2 is a perspective view showing the inside of an insert section of the endoscope.

FIG. 2 is a perspective view showing the inside of the insert section 11. Internal components are incorporated inside the insert section 11, such as a cylindrical channel tube 17 through which a treatment tool such as an ultrasonic probe and forceps, passes, an optical fiber 18 for illumination light which transmits illumination light to the illumination optical system, and wiring 19 for image pickup elements. Furthermore, a curved-shape detection sensor 100 is incorporated inside the insert section 11 to detect a curved shape of the insert section 11. The curved-shape detection sensor 100 includes a plurality of optical fibers 101, and these optical fibers 101 are arranged at least in the insert section 11. In this embodiment, the optical fibers 101 are fixed onto the outer surface of the channel tube 17 by displacement restraint sections 106 described later.

Of the internal components of the insert section 11, the channel tube 17 has the largest cross-sectional area and is thus hard to distort more than the other internal components. If an internal component for fixing the optical fibers 101 is subjected to distort, sensing parts 105 (described later) of the optical fibers 101 are displaced so that detection precision of a curved shape lowers. It is thus desirable that an internal component for fixing the optical fibers is hard to distort inside the insert section 11. In this embodiment, therefore, the optical fibers 101 are fixed in the channel tube 17. However, the internal component for fixing the optical fibers 101 is not limited to the channel tube 17 but may include a component that is displaced along the curve of the insert section 11, such as the optical fiber 18 for illumination light and the wiring 19 for image pickup elements, or a component that is curved along with the insert section 11.

[Curved-Shape Detection Sensor]

Figure 3:
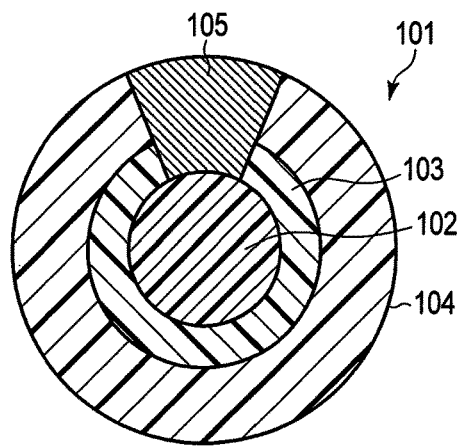
FIG. 3 is a cross-sectional view of an optical fiber that constitutes a curved-shape detection sensor.

FIG. 3 is a cross-sectional view of an optical fiber 101 that constitutes the curved-shape detection sensor 100. The curved-shape detection sensor 100 includes an optical fiber 101 having a core 102, a cladding 103 and a coating 104. As shown in FIG. 2, each of the optical fibers 101 includes one sensing part 105. As shown in FIG. 3, the sensing part 105 is formed by removing part of the coating 104 covering the outer surface of the cladding 103 and part of the cladding 103 covering the outer surface of the core 102 to expose the core 102 and then applying a light absorber on the exposed core 102. The light absorber absorbs part of light guided through the core 102 of the optical fiber 101. The sensing part 105 can be formed by any means other than the application of the light absorber if the sensing part 105 is mechanically attached to the core 102 such that they are formed integrally as one unit.

Figure 5:
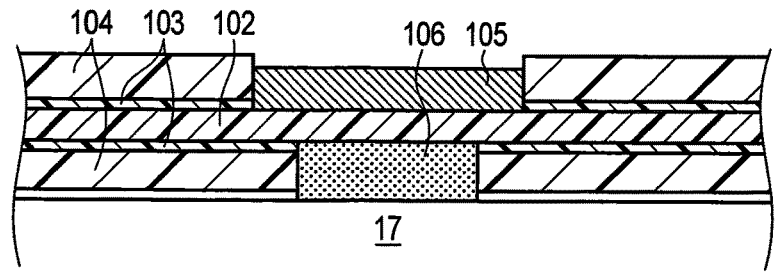
FIG. 5 is a longitudinal sectional view showing an optical fiber fixed to a channel tube by a displacement restraint section.
Figure 6:
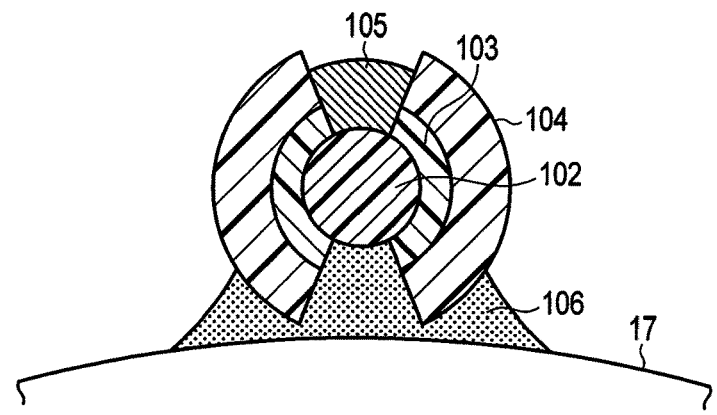
FIG. 6 is a cross-sectional view showing the optical fiber fixed to the channel tube by the displacement restraint section.

In FIG. 3, the outer surface of the coating 104 and that of the sensing part 105 are flush with each other in their radial directions; however, the thickness of the sensing part 105 in its radial direction can be set smaller than that of the coating 104 in its radial direction (see FIGS. 5 and 6, for example).

The light-emitting unit 21 that emits and guides light through the optical fiber 101 and the light-receiving unit 22 that receives light guided through the optical fiber 101 are connected to the proximal end of the optical fiber 101. In this embodiment, the light-emitting unit 21 and the light-receiving unit 22 are disposed in the apparatus main body 20; however, they can be disposed separately from the apparatus main body 20, disposed in the endoscope 10, or the like. A mirror 107 is disposed at the distal end of the optical fiber 101 (see FIGS. 24-26).

Referring again to FIG. 2, paired sensing parts 105$a$ and 105$b$ are respectively formed on two optical fibers 101$a$ and 101$b$ of the optical fibers 101 in the X-axis and Y-axis directions shown in FIG. 2 in order to detect curved shapes in two directions orthogonal to the longitudinal direction (insertion direction) and perpendicular to each other, namely, in the X-axis and Y-axis directions. A plurality of optical fibers 101 are disposed in such a manner that the paired sensing parts 105$a$ and 105$b$ are located in the same position in the longitudinal direction of the insert section 11.

Figure 4A:
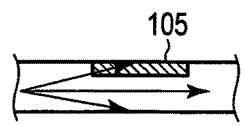
FIG. 4A is an illustration of one example of light passing by a sensing part of the optical fiber.
Figure 4B:
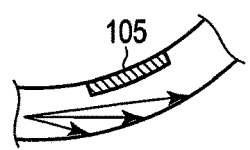
FIG. 4B is an illustration of one example of light passing by a sensing part of the optical fiber.
Figure 4C:
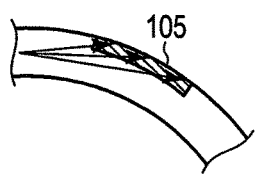
FIG. 4C is an illustration of one example of light passing by a sensing part of the optical fiber.

FIGS. 4A-4C are schematic views showing light passing by the sensing part 105 of the optical fiber 101. When the optical fiber 101 is straight, light guided through the optical fiber 101 is partly absorbed by the light absorber of the sensing part 105 (FIG. 4A). When the sensing part 105 is curved inwardly, light applied to the sensing part 105 decreases and thus the amount of light absorbed by the sensing part 105 becomes small (FIG. 4B). In other words, the amount of light transmitted through the optical fiber 101 becomes large. On the other hand, when the sensing part 105 is curved outwardly, light applied to the sensing part 105 increases and thus the amount of light absorbed by the sensing part 105 becomes large (FIG. 4C). In other words, the amount of light transmitted through the optical fiber 101 becomes small. Thus, the sensing part 105 contributes to detect an amount of curvature on the basis of the amount of light transmitted through the optical fiber 101 in accordance with the curve of the optical fiber 101.

The light passed through the sensing part 105 is reflected by the mirror 107 at the distal end of the optical fiber 101, guided through the optical fiber 101 in the opposite direction, and received by the light-receiving unit 22. The light-receiving unit 22 outputs the amount of received light to the computation unit 23.

[Computation Unit]

The computation unit 23 computes a curved shape of the insert section 11 of the endoscope 10 into which the curved-shape detection sensor 100 is incorporated, on the basis of the amount of received light output from the light-receiving unit 22. Prior to the computation, for example, the following expression is pre-known, showing a relationship between a variation in the amount of light transmitted through the optical fiber 101 (a difference between the amount of light emitted from the light-emitting unit 21 and the amount of light received by the light-receiving unit 22) $\Delta l$ and the amount of curvature $\varphi$ of the detector 105.

$$\varphi = f(\Delta l) \quad \text{expression 1}$$

From expression 1, an amount of curvature is computed for each of the sensing parts 105. Then, a curved shape of the insert section 11 is computed from the amount of curvature for each of the sensing parts 105 and the known data indicating an interval between the sensing parts 105. The amount of curvature need not be computed directly from expression 1, but can be computed by storing an equivalent conversion table in the computation unit 23 and then calling from the conversion table.

[Display Unit]

The display unit 30 is detachably connected to the apparatus main body 20. The display unit 30 displays an image in the insertion target 200 picked up by the endoscope 10 and a curved shape of the insert section 11 computed by the computation unit 23.

Next, fixation of an optical fiber 101 to the channel tube 17 will be described.

FIGS. 5 and 6 are a longitudinal sectional view and a cross-sectional view showing an optical fiber 101 fixed to the channel tube 17, respectively. In the optical fiber 101, the core 102 and the cladding 103 are brought into intimate contact with each other such that they do not move to each other; however, the optical fiber 101 can be configured to allow movement between the cladding 103 and the coating 104. Thus, even though only the coating 104 is fixed to the channel tube 17, the core 102 and the cladding 103 may move in relation to the channel tube 17. Therefore, for example, when the core 102 rotates, the sensing part 105 that is formed integrally with the core 102 also rotates, with the result that the detection precision of the amount of curvature can be lowered.

In this embodiment, therefore, part of the coating 104 and that of the cladding 103 which are opposed to the sensing part 105 are removed to form an opening to expose the core 102, and the opening to which the core 102 is exposed is filled with an adhesive to form a displacement restraint section 106. In other words, the displacement restraint section 106 restrains a relative displacement of the core 102 by adhesion to the channel tube 17. Thus, the displacement of the core 102 relative to the channel tube 17 is directly restrained.

Material whose refractive index is lower than that of the core 102 is used as the adhesive to form the displacement restraint section 106 that contacts the core 102 so as to reflect all of the light guided through the core 102, or to perform an alternative function of the removed part of the cladding. Furthermore, it is desirable that the adhesive be made of soft materials not to disturb the optical fiber 102 from being curved.

If the displacement restraint section 106 is long in the longitudinal direction of the optical fiber 101 or the displacement restraint section 106 contacts a plurality of portions in a wide range, it is likely that tension will be applied to the optical fiber 101 to damage the optical fiber when the channel tube 17 is curved together with the insert section 11. The displacement restraint section 106 is thus formed narrowly only in one portion in the longitudinal direction of the optical fiber 101 within a range to be capable of maintaining adhesion strength.

According to this embodiment, the displacement restraint section 106 directly restrains a displacement of the core 102 relative to the channel tube 17 that is displaced along the curvature of the insert section 11. In other words, the displacement restraint section 106 directly restrains a relative displacement of the sensing part 105 that is formed integrally with the core 102 with respect to the insert section 11. Therefore, the sensing part 105 is displaced along the curvature of the insert section 11 without moving or rotating in the longitudinal direction of the insert section 11, thus making it possible to improve detection precision of the curved shape of the insert section 11.

Since, moreover, the displacement restraint section 106 restrains a displacement of the core 102 relative to the channel tube 17 by adhesion, the displacement of the core 102 and channel tube 17 can be restrained even though the opening formed by removing the coating 104 and cladding 103 is a relatively small one whose width is, for example, approximately 100 μm. The displacement of the core 102 and channel tube 17 can also be restrained even in a limited space in the insert section.

If, furthermore, the adhesive of the displacement restraint section 106 is made of material whose refractive index is lower than that of the core 102, all of the light guided through the core 102 can be reflected. It is thus possible to prevent a loss of light guided through the core 102 due to the displacement restraint section 106.

The displacement restraint section 106 need not be adhered by an adhesive. If two members are chemically combined, the displacement restraint section 106 can be adhered by a mixed layer formed by deriving from the materials of the core 102 and the channel tube 17. Or, the core 102 and the channel tube 17 can be mechanically fixed to restrain the displacement of the core 102 by not only the adhesion but also pressing, absorption, fusion described later, or the like. In FIGS. 5 and 6, the channel tube 17 and the coating 104 do not contact each other in portions other than where the displacement restraint section 106 is provided, but they can contact each other if the displacement restraint section 106 has only to fix the core 102 to the channel tube 17 to directly restrain the displacement of the core 102 relative to the channel tube 17.

Figure 7:
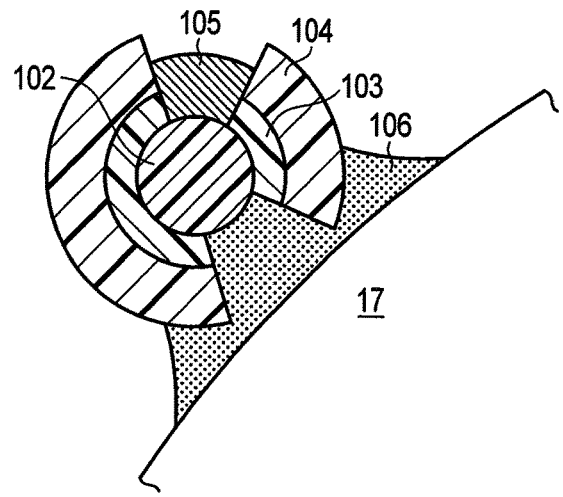
FIG. 7 is a cross-sectional view showing the optical fiber fixed to the channel tube by the displacement restraint section.

The position of the displacement restraint section 106 around the central axis of the optical fiber 101 with respect to the position of the sensing part 105 is not limited to a 180-degree difference position, but depends upon the relationship in position between the optical fiber 101 and the internal components of the insert section 11. For example, the sensing part 105 and the displacement restraint section 106 can be located in a position displaced from their opposite positions, as shown in FIG. 7.

The sensing part 105 can be located in a different position in the longitudinal direction of the optical fiber 101 with respect to the displacement restraint section 106.

If, however, the sensing part 105 is located in a position distant from the position of the displacement restraint section 106 in the longitudinal direction of the optical fiber 101, it is likely that the optical fiber 101 will be twisted and the sensing part 105 will rotate with respect to the displacement restraint section 106. In other words, the sensing part 105 is likely to rotate with respect to the insert section 11, which lowers detection precision of an amount of curvature. It is thus desirable that the displacement restraint section 106 be located in the same position as that of the sensing part 105 in the longitudinal direction of the optical fiber 101 or close to the sensing part within a range that allows the sensing part 105 to be rotated by the twist.

Figure 8:
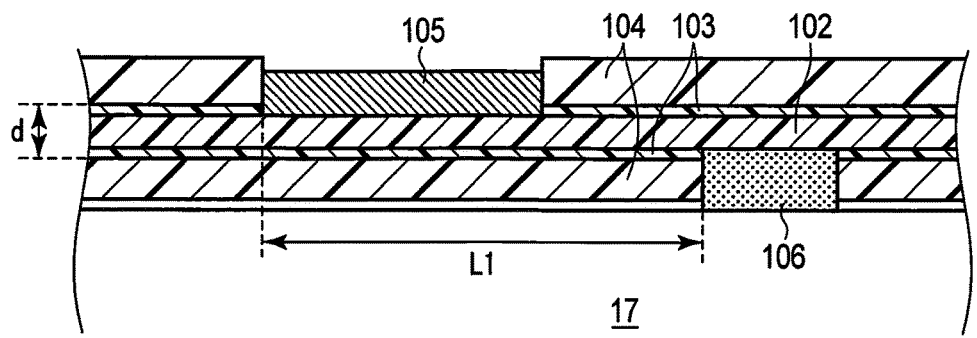
FIG. 8 is a longitudinal sectional view showing a relationship in position between the displacement restraint section and the sensing part in the longitudinal direction of the optical fiber.

As shown in FIG. 8, the position close to the sensing part indicates the range of $L_1$ that satisfies the following expression 2 where the length $L_1$ from one end of the displacement restraint section 106 on the sensing part side to one end of the sensing part 105 different from the displacement restraint section side.

$$L_1 \leq 240 \times d [\text{mm}] \qquad \text{expression 2}$$

If the position of the displacement restraint section 106 relative to the sensing part 105 falls within the range that allows the sensing part 105 to be rotated by the twist of the optical fiber 101, the detection precision of the amount of curvature can be improved.

Figure 9:
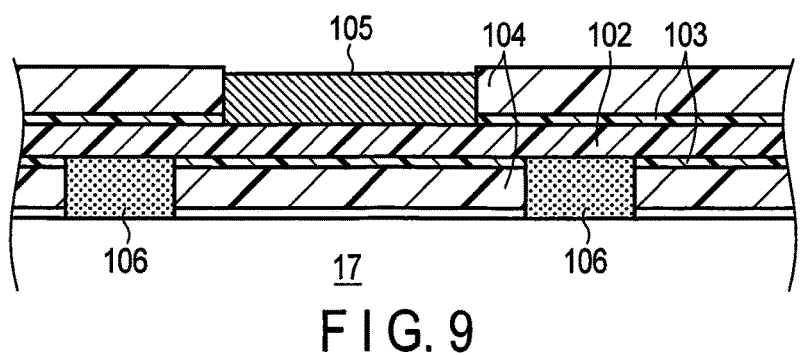
FIG. 9 is a longitudinal sectional view showing an optical fiber fixed to a channel tube by a plurality of displacement restraint sections.

In the foregoing descriptions, one displacement restraint section 106 is formed for the sensing part 105; however, a plurality of displacement restraint sections 106 can be provided as shown in FIG. 9 if the optical fiber is not damaged due to tension.

Figure 10:
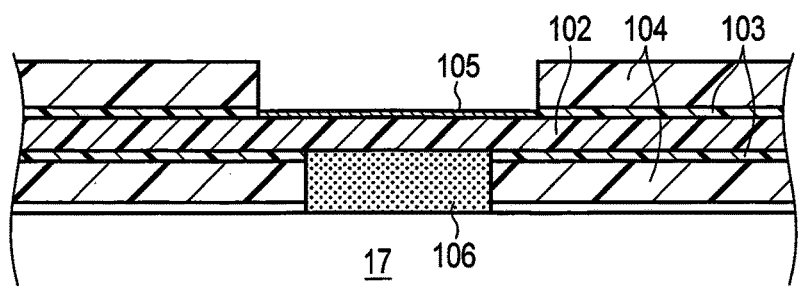
FIG. 10 is a longitudinal sectional view showing an optical fiber provided with a sensing part whose thickness is equal to or smaller than that of a cladding.
Figure 11:
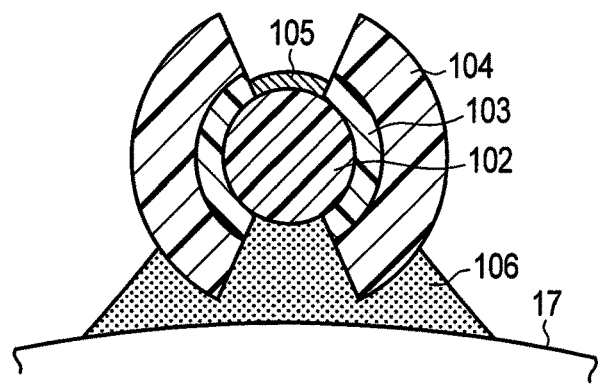
FIG. 11 is a cross-sectional view showing the optical fiber provided with a sensing part whose thickness is equal to or smaller than that of a cladding.

As shown in FIGS. 10 and 11, the thickness of the light absorber of the sensing part 105 can be set equal to or smaller than that of the cladding 103. Accordingly, even though the coating 104 is displaced relative to the core 102 and the cladding 103, the sensing part 105 does not receive any external force from the coating 104. Therefore, the possibility that the sensing part 105 will be displaced and come off becomes low, and an amount of curvature can stably be detected.

Figure 12A:
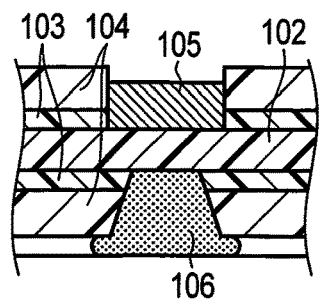
FIG. 12A is a schematic longitudinal sectional view showing an optical fiber fixed to a channel tube by a displacement restraint section.
Figure 12B:
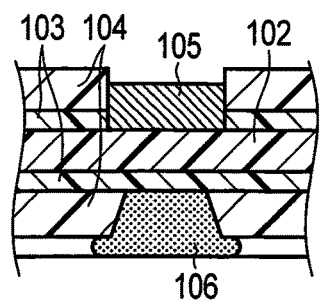
FIG. 12B is a schematic longitudinal sectional view showing an optical fiber fixed to a channel tube by a displacement restraint section.
Figure 12C:
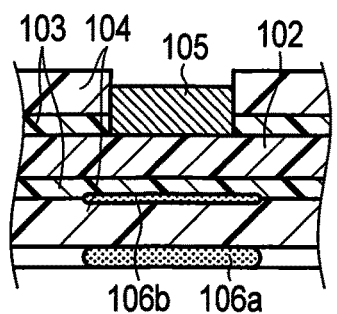
FIG. 12C is a schematic longitudinal sectional view showing an optical fiber fixed to a channel tube by displacement restraint sections.

FIGS. 12A-12C are schematic longitudinal sectional views showing an optical fiber 101 fixed to the channel tube 17. In the foregoing configuration, as shown in FIG. 12A, the coating 104 and the cladding 103 are partly removed to form an opening, and the core 102 and the channel tube 17 are brought into direct contact with each other by the displacement restraint section 106 to restrain the displacement of the core 102 relative to the channel tube 17. As shown in FIG. 12B, however, the cladding 103 is left and the coating 104 is partly removed to form an opening, and the opening is filled with an adhesive to form the displacement restraint section 106, with the result that the cladding 103 and the channel tube 17 can be adhered to each other.

Since the core 102 and the cladding 103 are brought into intimate contact with each other even in the foregoing configuration, the displacement of the core 102 relative to the channel tube 17 can indirectly be restrained via the cladding 103. In this configuration, the cladding 103 is not removed; thus, there is no loss of light when light passes by the displacement restraint section 106. It is therefore possible to remove restrictions on the refractive index of an adhesive serving as the displacement restraint section 106.

Figure 13:
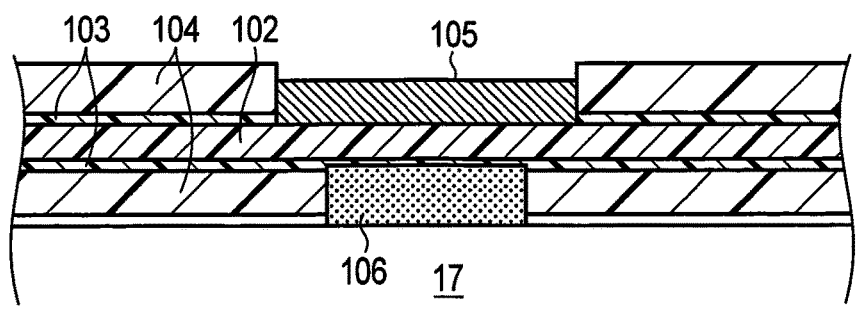
FIG. 13 is a longitudinal sectional view showing an optical fiber fixed to a channel tube by a displacement restraint section.

There is a case where it is difficult to form an opening only in the coating 104 as shown in FIG. 12B depending on the materials of the cladding 103. In this case, as shown in FIGS. 13 and 14, the displacement restraint section 106 can be formed by partly removing the coating 104 and also partly removing the cladding 103 in the radial direction of the opening. Thus, the degree of difficulty in forming the displacement restraint section 106 is lowered, or the displacement restraint section 106 can easily be formed.

As shown in FIG. 12C, a displacement restraint section 106a can be formed between the coating 104 and the channel tube 17 without opening the coating 104 and a displacement restraint section 106b can be formed substantially in the same position of the displacement restraint section 106a in the longitudinal direction and between the cladding 103 and the coating 104 by injecting an adhesive by, e.g. an injector.

Even in the foregoing configuration, the core 102 and the cladding 103 are brought into intimate contact without moving to each other, the cladding 103 and the coating 104 are adhered by the displacement restraint section 106b, and the channel tube 17 and the coating 104 are adhered by the displacement restraint section 106a. Thus, the displacement of the core 102 relative to the channel tube 17 can indirectly be restrained via the cladding 103 and the coating 104. If an opening is formed in the coating 104 and the cladding 103, the strength of the optical fiber 101 decreases; however, in this configuration, no opening is formed and the displacement restraint sections 106a and 106b can be formed without decreasing the strength of the optical fiber 101.

It is described above that an adhesive is injected by, e.g. an injector. As shown in FIG. 15, however, the cladding 103 and the coating 104 can be adhered by forming an opening in the coating 104 in a position other than the position in which the coating 104 is adhered to the channel tube 17, injecting an adhesive whose viscosity is low from the opening, and causing the adhesive to spread between the cladding 103 and the coating 104.

Figure 16A:
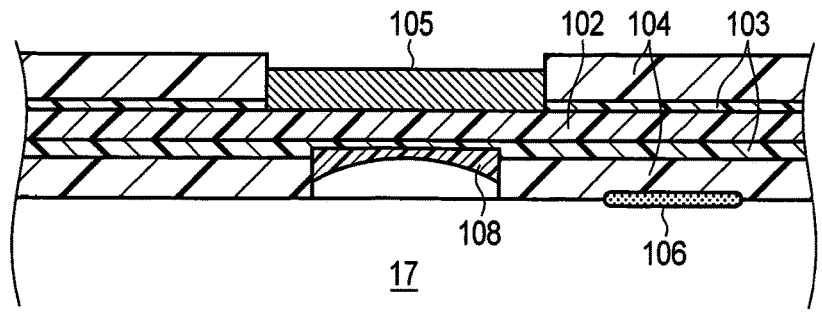
FIG. 16A is a longitudinal sectional view showing an optical fiber fixed to a channel tube by displacement restraint sections.

Or, as shown in FIG. 16A, in order to form a displacement restraint section 108 between the coating 104 and the cladding 103, the coating 104 is opened by applying external energy of, e.g. a laser and heating, and the cladding 103 is partly cut to fuse the coating 104 and the cladding 103 together. Thus, the displacement restraint section 108 is formed by the fusion and accordingly the coating 104 and the cladding 103 are formed integrally with each other. Then, the coating 104 and the channel tube 17 are adhered by the displacement restraint section 106a. Therefore, the coating 104 and the cladding 103 can be adhered without using an adhesive as the displacement restraint section 106b.

Figure 16B:
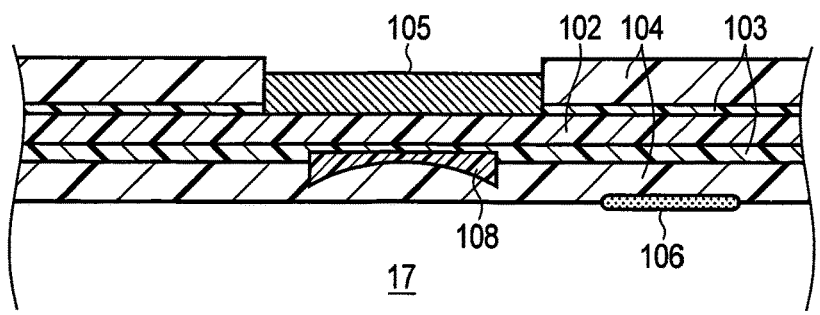
FIG. 16B is a longitudinal sectional view showing an optical fiber fixed to a channel tube by displacement restraint sections.

As shown in FIG. 16B, the coating 104 and the cladding 103 can be fused together without forming an opening in the coating 104 by obtaining focus of a laser beam on the contact surface between the coating 104 and the cladding 103 to increase the energy density of laser beam and decreasing the energy density of the laser beam in another portion.

Figure 17:
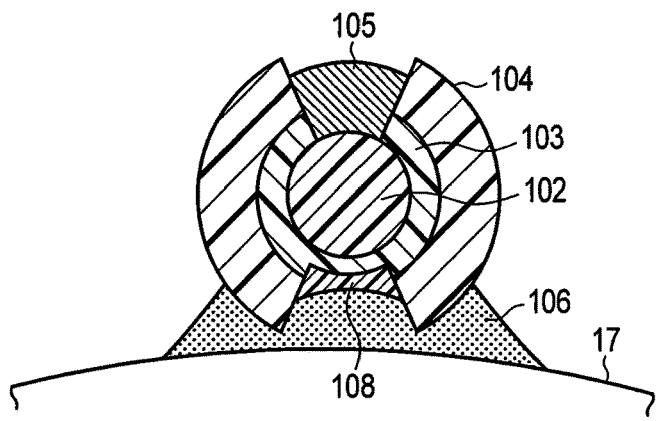
FIG. 17 is a cross-sectional view showing an optical fiber fixed to a channel tube by displacement restraint sections.

As shown in FIGS. 17 and 18, the displacement restraint section 108 formed by the fusion and the channel tube 17 can directly be adhered to each other.

The displacement restraint section 106a (displacement restraint section 106) between the channel tube 17 and the coating 104 and the displacement restraint section 106b (displacement restraint section 108) between the cladding 103 and the coating 104 need not be formed in the same position in the longitudinal direction of the optical fiber 101, but can be formed in different positions or can partly overlap each other if they are fall within a range that allows the sensing part 105 to be rotated by twist of the optical fiber 101.

The range that allows the sensing part 105 to be rotated by twist of the optical fiber 101 is a range of $L_2$ that satisfies the following expression 3 where the length between adjacent ends of the displacement restraint sections 106a and 106b is $L_2$ and the thickness of the coating 104 is t.

$$L_2 \leq 400 \times t \text{[mm]} \qquad \text{expression 3}$$

If the position of the displacement restraint section 106 with respect to the sensing part 105 falls within a range that allows the sensing part 105 to be rotated by twist of the optical fiber 101 as described above, detection precision of the amount of curvature can be improved.

A plurality of displacement restraint sections 106a can be present between the channel tube 17 and the coating 104 as shown in FIG. 20 if the optical fiber 101 is not damaged by tension applied thereto. A plurality of displacement restraint sections 106b can also be present. Furthermore, both displacement restraint sections 106a and 106b can also be present.

It has been described that the displacement restraint section 106 is provided separately from the sensing part 105, but the sensing part 105 and the displacement restraint section 106 can be formed integrally with each other, or the sensing part 105 can be formed to also serve the displacement restraint section 106, as shown in FIG. 21. In these configurations, the coating 104 and the cladding 103 are partly removed to form an opening and the opening is filled with a light absorber having an adhesive force. After that, the core 102 of the opening and the channel tube 17 are directly adhered to each other to restrain the displacement of the core 102 relative to the channel tube 17. Thus, one opening can be caused to have both the functions of the sensing part 105 and the displacement restraint section 106, thus making it possible to simplify the configuration.

Figure 23:
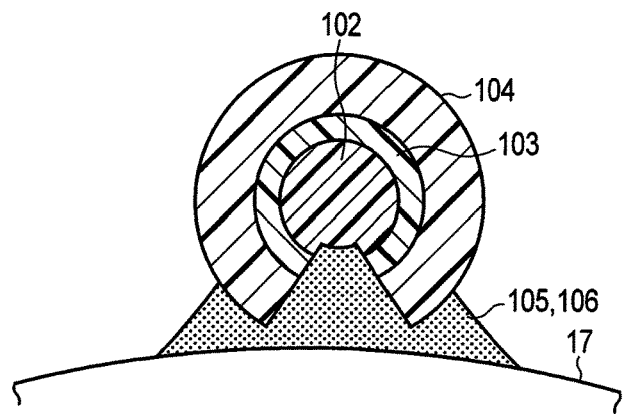
FIG. 23 is a cross-sectional view showing an optical fiber in which a sensing part and a displacement restraint section are formed integrally as one unit.

When the sensing part 105 and the displacement restraint section 106 are formed integrally with each other, the sensing part 105 and the displacement restraint section 106 can be formed by partly removing the coating 104 and the cladding 103 to form an opening and partly cutting the core 102 in the radial direction of the opening, as shown in FIGS. 22 and 23. Thus, the amount of light absorbed by the sensing part 105 increases and thus detection sensitivity to the amount of curvature can be improved.

Figure 24:
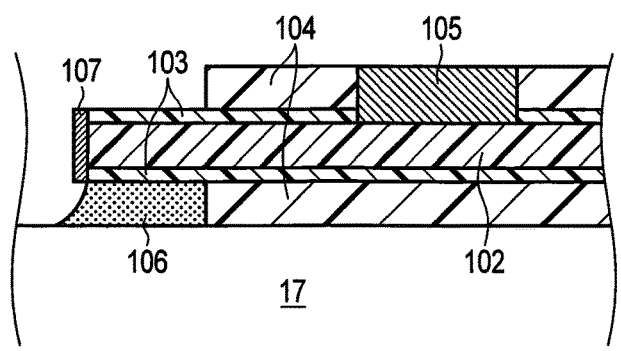
FIG. 24 is a longitudinal sectional view showing an optical fiber fixed to a channel tube by a displacement restraint section at a distal end of an optical fiber.

In the foregoing descriptions, the displacement restraint section 106 is formed halfway through the optical fiber 101. However, a position in which the displacement restraint section 106 is formed is not limited to the halfway position, but as shown in FIG. 24, it can be formed at the side end portion of the optical fiber 101 to include part of all thereof. The side end portion of the optical fiber 101 corresponds to a range from the side end portion of the coating 104 to that of the cladding 103 and the core 102. In FIG. 24, the cladding 103 and the channel tube 17 are adhered by the displacement restraint section 106; however, the core 102 and the channel tube 17 can be adhered by, e.g. a low refractive index adhesive by removing the cladding 103.

Figure 25:
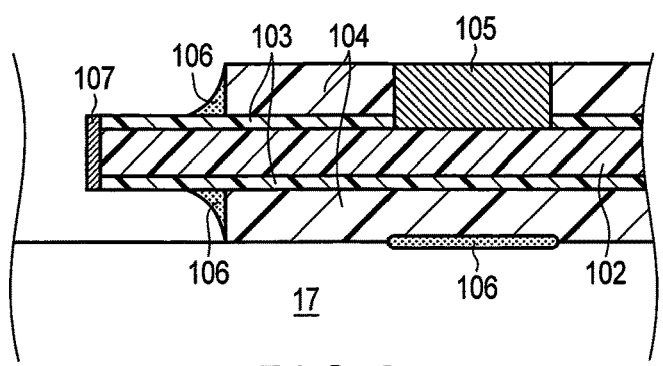
FIG. 25 is a longitudinal sectional view showing an optical fiber fixed to a channel tube by a displacement restraint section at a distal end of an optical fiber.

Furthermore, as shown in FIG. 25, a displacement restraint section 106 can be formed at the side end portion of the optical fiber to adhere the cladding 103 and the coating 104 to each other and a displacement restraint section 106 can be formed at a different position to adhere the coating 104 and the channel tube 17 to each other.

Figure 26:
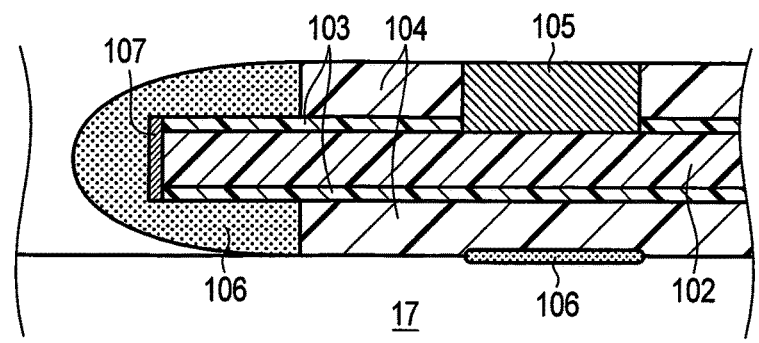
FIG. 26 is a longitudinal sectional view showing an optical fiber fixed to a channel tube by a displacement restraint section at a distal end of an optical fiber.

A mirror 107 is disposed at the side end portion of the optical fiber 101 to reflect light guided through the core 102. It is desirable that the mirror 107 be protected by, e.g. resin because it easily comes off and is damaged due to an external force. As shown in FIG. 26, therefore, the cladding 103 and the coating 104 can be adhered by applying an adhesive to cover the mirror 107 to form a displacement restraint section 106, and a displacement restraint section 106 can be formed at a different position to adhere the coating 104 and the channel tube 17. It is thus possible to fulfill a displacement restraint function and a mirror protection function at once by adhesion of the displacement restraint section 106.

It has been described that one sensing part 105 is provided for one optical fiber 105; however, a plurality of sensing part 105 can be provided for one optical fiber 101. For example, if a plurality of sensing parts 105 are formed by applying light absorbers having different wavelength characteristics, the amount of light of different wavelengths varies with a curved state of each sensing part 105. It is thus possible to detect a variation in the amount of light of each wavelength and compute the amount of curvature of its corresponding sensing part 105.

Figure 27:
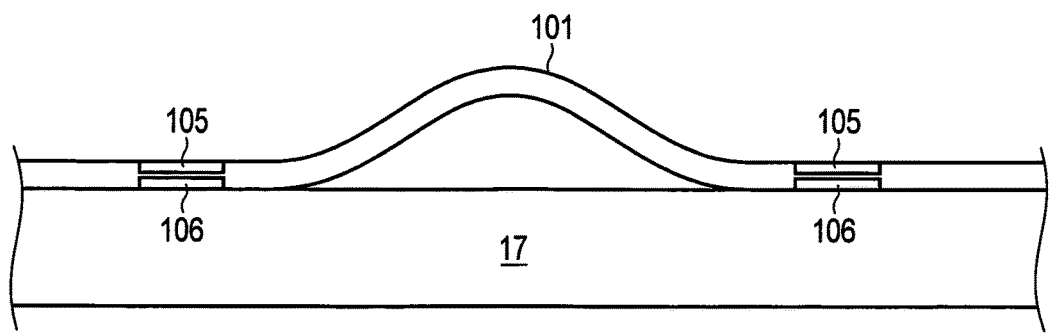
FIG. 27 is a longitudinal side view showing an optical fiber bent between one sensing part and its corresponding displacement restraint section and other sensing part and its corresponding displacement restraint section.

When a plurality of sensing parts 105 are provided for one optical fiber 101, if a plurality of displacement restraint sections 106 are provided to correspond to each sensing parts 105, the optical fiber 101 are fixed at a plurality of portions. It is thus likely that when the channel tube 17 is curved together with the insert section 11, the optical fiber 101 will be damaged due to tension applied thereto. Therefore, as shown in FIG. 27, the optical fiber 101 extending between two displacement restraint sections 106 is slackened to such a degree that no tension is applied to the optical fiber 101 even though the channel tube 17 is curved, and adhered to both the displacement restraint sections 106 to restrain the displacement of the core 102 relative to the channel tube 17 along the curve of the insert section 11. Thus, even though the position of the optical fiber 101 is fixed by the displacement restraint sections 106, no tension is applied to the optical fiber 101 by the curvature, thus making it difficult to damage the optical fiber.

In the foregoing descriptions, the displacement of, e.g. a core can be restrained directly or indirectly by the displacement restraint section 106 for the internal components of the insert section 11, for example, the cylindrical channel tube 17, the optical fiber 18 the wiring 19 for image pickup elements, and the like. However, it can be restrained using pieces 111 as shown in FIG. 28.

Figure 28:
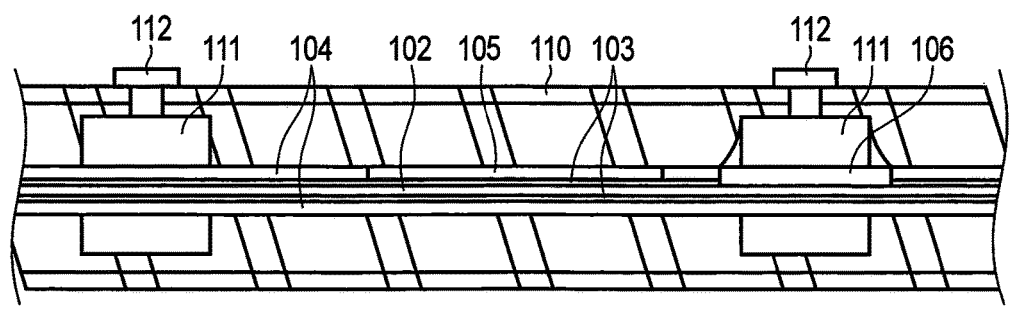
FIG. 28 is a schematic view showing a displacement restraint mechanism using liner tubes and pieces.

FIG. 28 is a schematic view showing a displacement restraint mechanism using liner tubes 110 and pieces 111. One of the two pieces 111 is disposed before a sensing part 105 and the other piece 111 is disposed after the sensing part 105, and the displacement of one of the pieces 111 relative to the core 102 is restrained directly or indirectly by the displacement restraint section 106. The displacement restraint section 106 may have any one of the configurations shown in FIGS. 12A-12C. The other piece 111 is not provided with a displacement restraint section 106 to prevent tension from being applied to the optical fiber 101 by the curvature, but the optical fiber 101 is disposed slidably with respect to the pieces 111. The pieces 111 are each screwed into the liner tube 110 by a screw 112. The liner tube 110 is a spiral, metallic tube.

Adopting the above displacement restraint mechanism, the curved-shape detection sensor 100 can be formed as a unit and becomes easy to handle. The liner tube 110 incorporating the optical fiber 101 is attached to, e.g. a structure in the curved portion 14, or it can be inserted and incorporated into the channel tube 17.

The present invention is not limited to the foregoing embodiment described above, but it is evident to a person with ordinary skill in the art that various improvements and modifications can be made without departing from the subject matter of the present invention.

REFERENCE SIGNS LIST

1 . . . Endoscope apparatus, 10 . . . Endoscope, 11 . . . Insert section, 12 . . . Operation unit main body, 13 . . . Cord section, 14 . . . Curved portion, 15 . . . Flexible tubular portion, 16 . . . Operation knob, 17 . . . Channel tube, 18 . . . Optical fiber for illumination light, 19 . . . Wiring for image pickup elements, 20 . . . Apparatus main body, 21 . . . Light-emitting unit, 22 . . . Light-receiving unit, 23 . . . Computation unit, 30 . . . Display unit, 100 . . . Curved-shape detection sensor, 101 . . . Optical fiber, 102 . . . Core, 103 . . . Cladding, 104 . . . Coating, 105 . . . Sensing part, 106, 106a, 106b . . . Displacement restraint section, 107 . . . Mirror, 108 . . . Displacement restraint section, 110 . . . Liner tube, 111 . . . Piece, 112 . . . Screw

What is claimed is:

1. An insertion apparatus comprising:
a flexible insert section configured to be inserted into an insertion target; and
a curved-shape detection sensor configured to detect a curved shape of the insert section,
wherein the curved-shape detection sensor comprises an optical fiber including at least a core, a cladding covering the core, a coating covering the cladding, and a sensing material mechanically attached to the core, the curved-shape detection sensor being configured to detect the curved shape,
the optical fiber is disposed at least in the insert section, and
the optical fiber includes at least one displacement restraint configured to directly or indirectly restrain a displacement of the sensing material relative to the insert section,
wherein the displacement restraint is formed in an opening formed by partly removing the coating and the cladding, and
the displacement restraint directly restrains a displacement of the core relative to an internal component of the insert section along curvature of the insert section.

2. The insertion apparatus according to claim 1, wherein the sensing material includes a light absorber that absorbs part of light guided through the core of the optical fiber,
the light absorber has an adhesive force, and
the sensing material also serves as the displacement restraint.

3. The insertion apparatus according to claim 1, wherein the displacement restraint restrains a displacement of the sensing material relative to the insert section indirectly through the cladding by restraining a displacement of the cladding relative to an internal component of the insert section along curvature of the insert section.

4. The insertion apparatus according to claim 3, wherein the displacement restraint restrains a displacement by adhering to the internal component.

5. The insertion apparatus according to claim 3, wherein the displacement restraint is disposed in a same position as the sensing material in a longitudinal direction of the optical fiber or close to the sensing material in the longitudinal direction of the optical fiber.

6. The insertion apparatus according to claim 3, wherein the displacement restraint is configured to contact the core and has a material whose refractive index is lower than that of the core.

7. The insertion apparatus according to claim 3, wherein the displacement restraint comprises a plurality of displacement restraints, and
the optical fiber in a range between the plurality of displacement restraints is slackened to restrain a displacement of the core relative to an internal component of the insert section along curvature of the insert section.

8. The insertion apparatus according to claim 1, wherein the displacement restraint restrains a displacement by adhering to the internal component.

9. The insertion apparatus according to claim 1, wherein the displacement restraint is disposed in a same position as the sensing part in a longitudinal direction of the optical fiber or close to the sensing part in the longitudinal direction of the optical fiber.

10. The insertion apparatus according to claim 1, wherein the displacement restraint is configured to contact the core and has a material whose refractive index is lower than that of the core.

11. The insertion apparatus according to claim 1, wherein the displacement restraint comprises a plurality of displacement restraints, and
the optical fiber in a range between the plurality of displacement restraints is slackened to restrain a displacement of the core relative to an internal component of the insert section along curvature of the insert section.

* * * * *